United States Patent [19]

Math et al.

[11] Patent Number: 6,013,276
[45] Date of Patent: Jan. 11, 2000

[54] TRANSDERMAL MATRIX SYSTEM

[75] Inventors: Marie-Christine Math; Eric Teillaud, both of Talant; Bruno Bevan, Chevigny Saint Sauveur, all of France

[73] Assignee: Laboratoires D'Hygiene et de Dietetique, Paris, France

[21] Appl. No.: 09/043,760

[22] PCT Filed: Sep. 25, 1996

[86] PCT No.: PCT/FR96/01494

§ 371 Date: Mar. 26, 1998

§ 102(e) Date: Mar. 26, 1998

[87] PCT Pub. No.: WO97/11687

PCT Pub. Date: Apr. 3, 1997

[30] Foreign Application Priority Data

Sep. 27, 1995 [FR] France .................................. 95 11326

[51] Int. Cl.$^7$ .................................................. A61F 13/02
[52] U.S. Cl. ........................ 424/448; 424/443; 424/448; 424/449; 424/487
[58] Field of Search .................... 424/448, 449, 424/443, 487

[56] References Cited

U.S. PATENT DOCUMENTS 5,286,490   2/1994   Goldberg ................................ 424/448
5,453,279   9/1995   Lee et al. .............................. 424/448
5,605,702   2/1997   Teillaud et al. ......................... 424/448

FOREIGN PATENT DOCUMENTS 0 055 360   7/1982   European Pat. Off. .
0 093 563   4/1983   European Pat. Off. .
0 279 982   8/1998   European Pat. Off. .
2 612 785   3/1987   France .
92/07589   5/1992   WIPO .

OTHER PUBLICATIONS

Patent Abstracts of Japan, vol. 16, No. 93 (C–917), Mar. 6, 1992 and JP 03 275619 A (NITSUSUI), Dec. 6, 1991.

*Primary Examiner*—Thurman K. Page
*Assistant Examiner*—Susan Tran
*Attorney, Agent, or Firm*—St. Onge Steward Johnston & Reens

[57] ABSTRACT

A novel transdermal matrix system for the percutaneous delivery of a hormone, including a carrier and an adhesive matrix, is disclosed. The matrix includes (a) 39–61 parts by weight of an ethylene/vinyl acetate copolymer, (b) 12–17 parts by weight of 2-octyldodecyl myristate, (c) 5–17 parts by weight of diethyl phthalate, (d) 10–16 parts by weight of a compound selected from N-alkyl-2-pyrrolidones, wherein the alkyl group is a $C_{4-15}$ group, and (e) 1–12 parts by weight of at least one hormone selected from the group consisting of oestrogenic and progestogenic components. A method for preparing said transdermal matrix system and the therapeutical use of said system are also disclosed.

23 Claims, 2 Drawing Sheets

TRANSDERMAL MATRIX SYSTEM

This application is a 371 of PCT/FR96/01494 filed Sep. 25, 1996.

FIELD OF THE INVENTION

The present invention relates to a novel matrix system for the transdermal administration of an estrogen component and/or a progestin component, said system being formed of a carrier and an adhesive matrix which is composed of an ethylene/vinyl acetate (EVA) copolymer and the specific association of three compounds, namely diethyl phthalate, 2-octyldodecyl myristate and an N-alkyl-2-pyrrolidone, and in which said estrogen component and/or said progestin component are dissolved.

The invention further relates to a method of preparing said matrix system and to its use in therapeutics.

PRIOR ART

Numerous systems for the transdermal administration of a hormone, particularly an estrogen component by itself, are currently available for the treatment of the symptoms of the menopause and osteoporosis in the context of treatments described as "hormone replacement therapy". These systems now include so-called "reservoir" systems, in which the active principle is dissolved in a solvent acting as a vector for transport through a microporous membrane towards the skin. This is the case of the device based on 17β-estradiol which is marketed by CIBA-GEIGY under the name ESTRADERM® TTS.

At the same time, so-called "matrix" systems exist in which the active principles are dissolved or dispersed in an adhesive matrix based on polymers such as EVA copolymers, acrylic copolymers, styrene/isoprene/styrene copolymers, etc. This is the case of the device based on 17β-estradiol which is marketed by LABORATOIRES FOURNIER S.C.A. under the name OESCLIM®.

On the other hand, the production of systems for the transdermal administration of an estrogen component and a progestin component in these matrix systems still presents numerous problems.

In fact, it is known that estrogens and progestins are products of very low solubility in the polymers used in the formulation of the matrix system. Furthermore, each of these active principles may be partially or totally incompatible with some of the constituents of the formulation (resins, solvents, plasticizers, polymers, skin absorption promoters). They may have different solubilities and stability temperatures and one of the two may recrystallize over time, degrade when used or be usable in the composition only at concentrations which are too low to achieve the desired therapeutic effect. Likewise, no universal skin absorption promoter exists for increasing the transdermal flux of all the active principles. Therefore, to administer different active principles, it is often necessary to use several promoters and/or solvents. Now, the introduction of any new substance may cause or raise new problems of irritation and cohesion or adhesion of the system.

In the same way, taken together, these constraints (compatibility, solubility) also affect the various constituents of the formulation other than the active principles, and therefore exacerbate the difficulties to be resolved.

Furthermore, these demands relating to skin tolerance, adhesion and cohesion of the system are compounded by dosage constraints. In general the active principles have different skin permeating abilities, meaning that each active principle has a different absorption flux. It therefore becomes very complicated to develop a formulation which enables the desired therapeutic dose of each active principle to be administered. In practice, it is very often impossible to develop such a formulation and the development leads to a dead end or to systems which are rather unsatisfactory and hence economically non-viable. This explains why no system of this type has yet been marketed.

In actual fact, the only currently available transdermal system for the administration of two hormones is a "reservoir" system based on 17β-estradiol and norethisterone acetate, which is marketed by CIBA-GEIGY under the name ESTRAGEST® TTS.

Those skilled in the art are also aware that estrogens and/or progestins are molecules which cannot easily pass through the skin barrier.

Thus the quantities of these active principles which are released to give the desired therapeutic effect are generally small compared with the initial quantities present in the transdermal devices, irrespective of their type, so the yields obtained are low.

Although matrix systems (where the matrix is based on ethylene/vinyl acetate (EVA) copolymer) for the administration of an estrogen component and/or a progestin component have already been described in published patent applications FR-A-2 612 785, EP-A-0 279 982, WO-A-92/07589 and EP-A-055 360, none of these publications either discloses or suggests the specific formulations of the invention which make it possible to overcome the disadvantages described above.

OBJECTS OF THE INVENTION

According to the invention, it is proposed to produce EVA-based matrix systems for the simultaneous administration of an estrogen component and a progestin component in order to solve the above-mentioned problems, said systems also giving excellent yields.

It is also proposed to produce such matrix systems for the administration of an estrogen component by itself or a progestin component by itself, said systems giving excellent yields.

According to a second aspect of the invention, it is proposed to provide a method of preparing these matrix systems.

According to yet another aspect of the invention, it is proposed to provide a use of such a matrix system in the treatment of the menopause and osteoporosis.

SUBJECT OF THE INVENTION

The above-mentioned objects are achieved by virtue of a novel technical solution wherein the matrix of the matrix system, which contains an estrogen component and/or a progestin component, essentially consists of EVA and the specific association of 3 compounds, namely diethyl phthalate, 2-octyldodecyl myristate and an N-alkyl-2-pyrrolidone.

More precisely, according to the invention, a transdermal matrix system for the transdermal administration of at least one hormone is proposed, said system, which comprises a carrier and an adhesive matrix, being characterized in that said matrix comprises:

(a) 39 to 61 parts by weight of ethylene/vinyl acetate copolymer, (b) 12 to 17 parts by weight of 2-octyldodecyl myristate, (c) 5 to 17 parts by weight of diethyl phthalate, (d) 10 to 16 parts by weight of a compound selected from N-alkyl-2-pyrrolidones in which the alkyl group is a $C_4$–$C_{15}$ group, and (e) 1 to 12 parts by weight of at least one hormone selected from the group consisting of estrogen components and progestin components.

According to a second aspect of the invention, another transdermal matrix system for the transdermal administration of at least one hormone is proposed, said system, which comprises a carrier and an adhesive matrix, being characterized in that said matrix comprises:

(a) 39 to 61 parts by weight of ethylene/vinyl acetate copolymer, (b) 12 to 17 parts by weight of 2-octyldodecyl myristate, (c) 5 to 17 parts by weight of diethyl phthalate, (d) 10 to 16 parts by weight of a compound selected from N-alkyl-2-pyrrolidones in which the alkyl group is a $C_4$–$C_{15}$ group, (e) 1 to 12 parts by weight of at least one hormone selected from the group consisting of estrogen components and progestin components, and (f) 1 to 10 parts by weight of a vinyl acetate/N-vinyl-2-pyrrolidone (abbreviated to VA/VP) copolymer.

According to the invention, a method of preparing said transdermal matrix system is also proposed, said method being characterized in that it comprises the steps wherein:

(α) the diethyl phthalate, the N-alkyl-2-pyrrolidone, the 2-octyldodecyl myristate, the hormone selected from the group consisting of estrogen components, progestin components and mixtures thereof, the VA/VP copolymer, if present in the formulation, and the EVA are successively introduced into a reactor at a temperature below the boiling point of the solvent or solvent system used, and the mixture obtained is stirred;

(β) the solvent or solvent system is then incorporated and the whole is stirred, still at the same temperature, until the EVA has totally dissolved and said mixture has become completely homogeneous;

(γ) the homogeneous mixture resulting from step (β) is coated onto a non-stick temporary carrier, at a temperature of between 50 and 70° C., to give a deposit of 50 to 300 g/m² on said carrier;

(δ) the coating obtained is heated to a temperature of between 40 and 80° C., depending on the boiling point of the solvent or solvent system, in order to evaporate the latter; and (ε) the resulting dry matrix is transferred to a final carrier.

It is also proposed to use a transdermal matrix system for obtaining a medicinal product intended for therapeutic use in treating the symptoms of the menopause or osteoporosis.

DRAWINGS

In the attached drawings, FIG. 4 shows the quantity (Q), expressed in μg/cm², of 17β-estradiol released as a function of time (t), expressed in hours, and FIGS. 1 to 3 show the yield (R), expressed in %, of 17β-estradiol or NETA (norethisterone acetate) as a function of time (t), expressed in hours.

More precisely, in these drawings:

A BRIEF DESCRIPTION OF THE DRAWINGS

Figure 3:
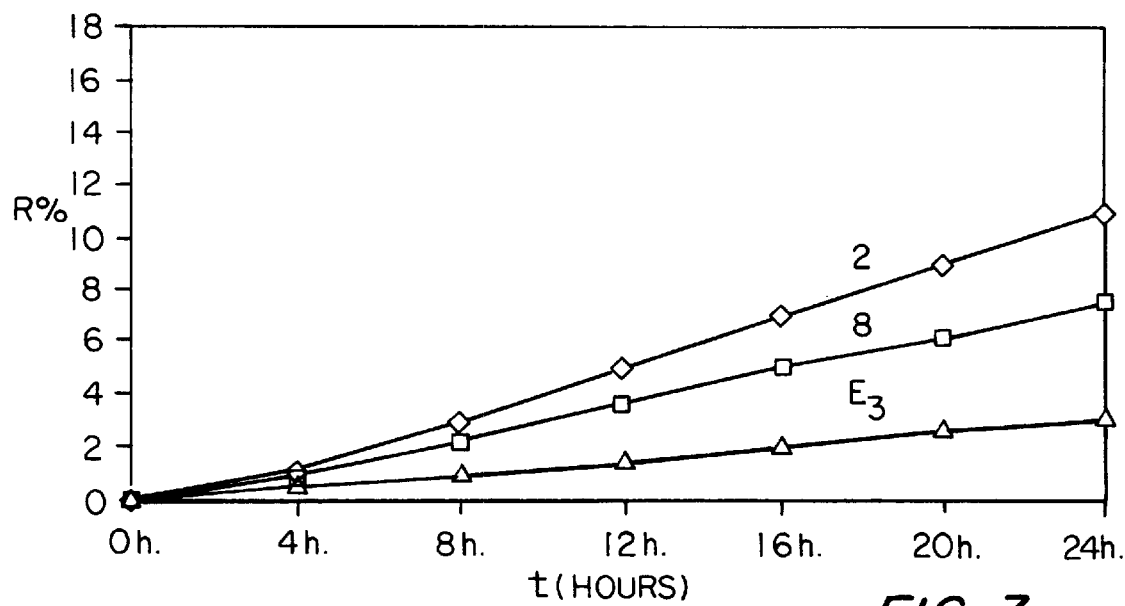
Figure 4:
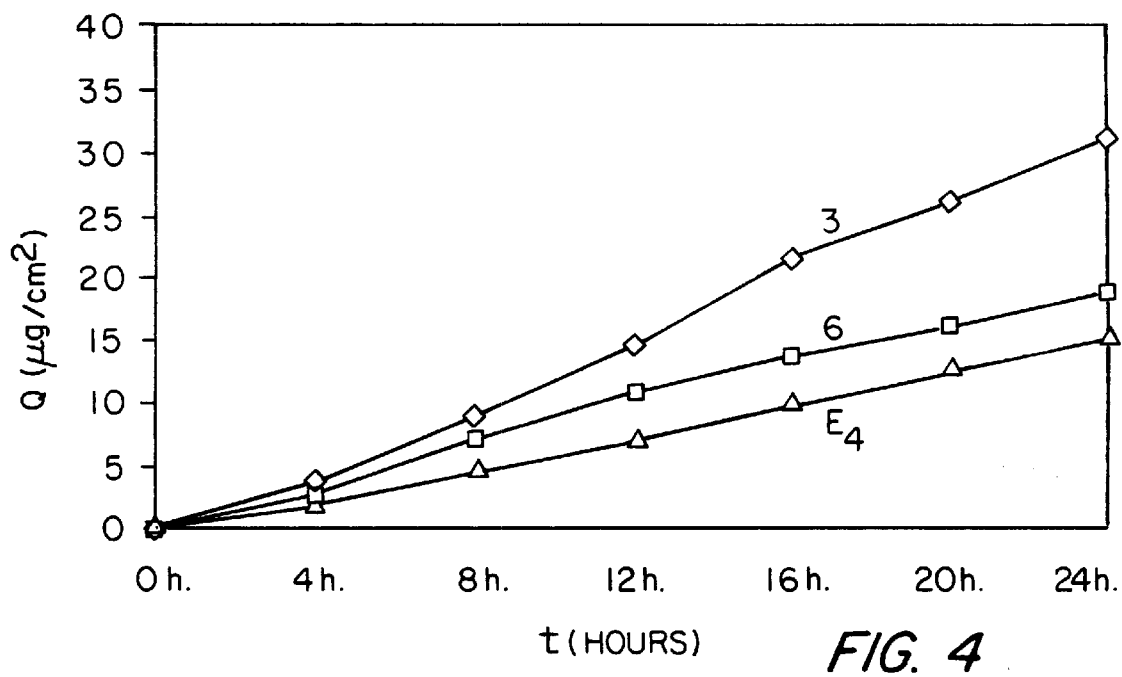

FIG. 3 shows the comparison (in the system R/t) between curves 2, 8 and $E_3$ relating to the yield of the release of 17β-estradiol, said curves being obtained respectively with the products of Examples 2 and 8 according to the invention and a reference transdermal product known under the name OESCLIM® and marketed by LABORATOIRES FOURNIER S.C.A. (identified here as $E_3$); and FIG. 4 shows the comparison (in the system Q/t) between curves 3, 6 and $E_4$ relating to the release of 17β-estradiol, said curves being obtained respectively with the products of Examples 3 and 6 according to the invention and OESCLIM® (identified here as $E_4$).

DETAILED DESCRIPTION OF THE INVENTION

It will be preferable to use an ethylene/vinyl acetate copolymer with a vinyl acetate content of between 30 and 75% by weight, in particular of the order of 45 to 60% by weight, based on the weight of the ethylene/vinyl acetate copolymer. A mixture of such EVAs with different molecular weights or different vinyl acetate contents may be used if appropriate.

The N-alkyl-2-pyrrolidones here include substances in which the alkyl group is a group formed of 4 to 15 carbon atoms, such as, for example, N-dodecyl-2-pyrrolidone and N-octyl-2-pyrrolidone. N-Dodecyl-2-pyrrolidone will be particularly preferred in the present invention. Within the framework of the present invention, hormone is understood as meaning the estrogen components and/or the progestin components.

Among the estrogen components which are suitable according to the invention, there may be mentioned particularly 17β-estradiol and estradiol derivatives, especially estradiol monoesters and diesters such as, for example, estradiol 17-acetate, estradiol 3,17-diacetate, estradiol 3-benzoate and estradiol 17-undecanoate, and estradiol derivatives alkylated in the 17-position, such as ethynylestradiol, ethynylestradiol 3-isopropylsulfonate, methylestradiol, quinestrol, mestranol and, if appropriate, mixtures thereof.

Among the progestin components which are suitable according to the invention, there may be mentioned particularly progesterone, medrogesterone and their derivatives (especially 17-hydroxyprogesterone acetate, medroxyprogesterone acetate), norethisterone and its derivatives (especially 17-norethisterone acetate), norpregnane, nomegestrol acetate and levonorgestrel.

According to the invention, it will be preferable to use 17β-estradiol as the estrogen component and 17-norethisterone acetate (NETA) as the progestin component.

Vinyl acetate/N-vinyl-2-pyrrolidone copolymer is understood here as meaning a copolymer with a vinyl acetate content of between 30 and 70% by weight, based on the weight of said copolymer. Such products are well known for their use as film-forming agents in aerosols and are marketed for example under the name "PVP/VA" by GAF CORPORATION, in the form of a powder in the case of the series PVP/VA-S or in the form of an ethanolic or isopropanolic solution in the case of the series PVP/VA-E and PVP/VA-I respectively, or under the name Kollidon VA by BASF. Among these products, particular preference will be given to the VA/VP copolymer marketed under the name PVP/VA-S-630, which contains 40% by weight of vinyl acetate, and the VA/VP copolymer marketed under the name Kollidon VA 64, which contains 37.7% by weight of vinyl acetate.

The carrier receiving the matrix may be any carrier which is generally used in occlusive or non-occlusive transdermal systems and which is impermeable to the constituents of the matrix. Preference will be given for example to a carrier in the form of a polyethylene, polypropylene or polyester film, a composite consisting of polyethylene and a vinyl acetate/ethylene copolymer, or a foam.

If necessary, an additional adhesive strip, for example a peripheral strip in the form of a ring, may be added to the system in order to optimize its adhesion properties.

In practical terms, the surface of the matrix which is not bonded to the carrier may be covered with a protective layer or film which can be peeled off before the device is used. Said device may itself be packaged in a leakproof protection such as, for example, a polyethylene-aluminum composite.

By virtue of the excellent yields of hormone release which it affords, the matrix system according to the invention has numerous advantages, which will now be described.

One advantage is the cost price, which is very appreciably lower than that of the devices currently on the market by virtue of using a smaller quantity of expensive hormone(s).

The risks of environmental pollution by these hormones when the product is disposed of after the treatment period are also reduced.

Only the formulations according to the invention, where an EVA copolymer is associated with 3 specific compounds, namely an N-alkyl-2-pyrrolidone, diethyl phthalate and 2-octyldodecyl myristate, enable these results to be achieved.

Furthermore, using a smaller quantity of estrogens and/or progestins while increasing the quantities released simplifies the development and production of the formulations forming the matrix of the devices.

In fact, this minimizes or eliminates the problems of the solubility of the hormones in the EVAs, as well as the risks of chemical or physical incompatibility with the other constituents of the matrix. The same applies to the problems of crystallization of the hormones and the instability of the devices over time, these latter phenomena being unacceptable for the validation and marketing of products for therapeutic purposes, such as transdermal systems.

All these advantages therefore ultimately make it possible to obtain an acceptable and marketable matrix system for the administration of an estrogen component and a progestin component, said system giving excellent yields.

If necessary, the cohesion of the device can be optimized by using a mixture of EVAs of different molecular weights. By the same token, the addition of the VA/VP copolymer makes it possible to optimize the adhesion properties and the solubility of the hormones in the matrix.

Surprisingly, it also makes it possible to minimize the skin irritation phenomena which some devices may exhibit.

The transdermal systems according to the invention are produced by the techniques generally employed by those skilled in the art, namely coating in the solvent phase or by the so-called "hot melt" technique, i.e. in the absence of a solvent.

In both cases, in the context of industrial production, large areas are coated and then cut up to give devices whose dimensions are adapted to the dose of active principle to be administered over a given time.

In the context of the so-called "solvent phase" technique, a method of preparing an adhesive matrix system according to the invention is proposed which comprises the following steps:

(α) the diethyl phthalate, the N-alkyl-2-pyrrolidone, the 2-octyldodecyl myristate, the hormone selected from the group consisting of estrogen components, progestin components and mixtures thereof the VA/VP copolymer, if present in the formulation, and the EVA are successively introduced into a mixer at a temperature below the boiling point of the solvent or solvent system used, for example ethyl acetate or an ethyl acetate/ethanol mixture, and the mixture obtained is stirred;

(β) the solvent or solvent system is incorporated and the whole is stirred, still at the same temperature, until the EVA has totally dissolved and the mixture has become completely homogeneous;

(γ) the resulting homogeneous mixture is coated, at a temperature of between 50 and 70° C., onto a non-stick temporary intermediate carrier, especially a siliconized polyester film, at a rate of 50 to 300 g/m$^2$;

(δ) the solvent or solvent system is evaporated off by heating to a temperature of between 40 and 80° C., preferably 60 to 80° C., depending on the boiling point of said solvent or solvent system; and (ε) the dry matrix resulting from step (δ) is transferred to the chosen final carrier.

The novel adhesive matrix device according to the invention is particularly useful for the treatment of osteoporosis, the symptoms of the menopause and the consequent cardiovascular risks, in the context of so-called "hormone replacement therapy", as well as for any treatment based on the transdermal administration of estrogens and/or progestins.

BEST MODE

The best mode of carrying out the invention consists in using a transdermal matrix system whose matrix contains the following for a total of 100 parts by weight:

(a) 54 parts by weight of ethylene/vinyl acetate copolymer, (b) 17 parts by weight of 2-octyldodecyl myristate, (c) 5 parts by weight of diethyl phthalate, (d) 16 parts by weight of N-dodecyl-2-pyrrolidone, (e$_1$) 2 parts by weight of 17β-estradiol, (e$_2$) 5 parts by weight of norethisterone acetate, and (f) 1 part by weight of a vinyl acetate/N-vinyl-2-pyrrolidone (VA/VP) copolymer, on the one hand, or (a) 62 parts by weight of ethylene/vinyl acetate copolymer, (b) 13 parts by weight of 2-octyldodecyl myristate, (c) 10 parts by weight of diethyl phthalate, (d) 10 parts by weight of N-dodecyl-2-pyrrolidone, (e) 3 parts by weight of 17β-estradiol, and (f) 2 parts by weight of a vinyl acetate/N-vinyl-2-pyrrolidone (VA/VP) copolymer, on the other hand, or (a) 53 parts by weight of ethylene/vinyl acetate copolymer, (b) 17 parts by weight of 2-octyldodecyl myristate, (c) 10 parts by weight of diethyl phthalate, (d) 13 parts by weight of N-dodecyl-2-pyrrolidone, (e) 6 parts by weight of norethisterone acetate, and (f) 1 part by weight of a vinyl acetate/N-vinyl-2-pyrrolidone (VA/VP) copolymer.

In these formulations, the EVA used advantageously has a vinyl acetate content of 60% by weight, based on the weight of said ethylene/vinyl acetate copolymer. The VA/VP copolymer in turn advantageously has a vinyl acetate content of 35 to 40% by weight, based on the weight of said VA/VP copolymer.

Other advantages and characteristics of the invention will be understood more clearly from the following description of Examples and comparative tests.

Of course, these details as a whole in no way imply a limitation but are given by way of illustration.

The following abbreviations have been used hereafter for the sake of convenience:

EVA: ethylene/vinyl acetate copolymer

Es: 17β-estradiol

NETA: norethisterone acetate

VA/VP: vinyl acetate/N-vinyl-2-pyrrolidone copolymer

EXAMPLE 1

0.62 g of 17β-estradiol, 1.2 g of NETA, 3 g of SURFADONE® LP 300 (N-dodecyl-2-pyrrolidone marketed by GAF CORPORATION), 3.9 g of 2-octyldodecyl myristate marketed by GATTEFOSSE (hereafter abbreviated to "ODM"), 3 g of diethyl phthalate and 40.5 g of ethyl acetate are introduced successively into a 250 ml beaker. The mixture obtained is heated to a temperature of between 65 and 75° C., with stirring. 18.3 g of LEVAPREN® 600 HV (an EVA copolymer with a content of vinyl acetate units of 60% by weight, marketed by BAYER) are then introduced in portions and the mixture obtained is stirred for about 50 minutes, with continued heating at between 65 and 75° C., until the EVA copolymer has completely dissolved. The dry extract is readjusted to 50% by weight and the mixture obtained is allowed to degas. It is coated onto a temporary siliconized polyester carrier at a temperature of between 65 and 75° C. so as to form a deposit of (100±10) g/m². The coating obtained is heated at 70° C. for at least 15 minutes in order to evaporate the solvent. The resulting matrix is then transferred to a final polyester carrier. After cutting to the desired size, the products are packaged in heat-sealable sachets.

EXAMPLE 2

The procedure is analogous to that of Example 1 except that 0.83 g of Es, 1.6 g of NETA, 4 g of SURFADONE® LP 300, 6 g of ODM, 6 g of diethyl phthalate, 54 g of ethyl acetate and 21.6 g of LEVAPREN® 600 HV (an EVA copolymer with a content of vinyl acetate units of 60% by weight, marketed by BAYER) are used in this case.

EXAMPLE 3

The procedure is analogous to that of Example 1 except that 0.62 g of Es, 1.2 g of NETA, 4.8 g of SURFADONE® LP 300, 5.1 g of ODM, 3 g of diethyl phthalate, 40.5 g of ethyl acetate and 15.3 g of LEVAPREN® 600 HV are used in this case.

EXAMPLE 4

The procedure is analogous to that of Example 1 except that a mixture of EVA copolymers is used in this case. 0.62 g of Es, 1.5 g of NETA, 3 g of SURFADONE® LP 300, 4.5 g of ODM, 3 g of diethyl phthalate, 40.5 g of ethyl acetate and a mixture of 14.4 g of LEVAPREN® 600 HV and 3 g of LEVAPREN® 400 (an EVA copolymer with a content of vinyl acetate units of 40% by weight, marketed by BAYER) are introduced.

EXAMPLE 5

201.6 g of diethyl phthalate, 101.3 g of SURFADONE® LP 300, 100.8 g of ODM, 20.7 g of Es, 40 g of NETA and 539.9 g of LEVAPREN® 500 HV (an EVA copolymer with a content of vinyl acetate units of 50% by weight, marketed by BAYER) are introduced into a reactor at room temperature and the whole is stirred. 1003.7 g of ethyl acetate are then incorporated and the mixture is heated at about 75° C., with stirring, until the EVA copolymer has completely dissolved. The mixture obtained is allowed to degas. It is coated onto a temporary siliconized polyester carrier at a temperature of 50° C. so as to form a deposit of (100±10) g/m². The coated product is then placed in a drying tunnel at a temperature varying from 60 to 80° C. in order to evaporate the solvent, and the resulting matrix is transferred to a final polyester carrier. After cutting to the desired size, the products are packaged in heat-sealable sachets.

EXAMPLE 6

130.5 g of ODM, 130.9 g of diethyl phthalate, 100.9 g of SURFADONE® LP 300, 20.7 g of Es, 40 g of NETA, 570.3 g of LEVAPREN® 600 HV and 10.1 g of PVP/VA-S-630 (a vinyl acetate/N-vinyl-2-pyrrolidone copolymer containing 40% by weight of vinyl acetate, marketed by GAF CORPORATION) are introduced into a reactor at 75° C. and the whole is stirred for 5 minutes. 989.9 g of ethyl acetate and 10.1 g of ethanol are then incorporated. The whole is stirred, still at 75° C., until the EVA copolymer has completely dissolved, and the mixture obtained is allowed to degas. It is coated onto a temporary siliconized polyester carrier at a temperature of 50° C. so as to form a deposit of (100±10) g/m². The coated product is then placed in a drying tunnel at a temperature varying from 60 to 80° C. in order to evaporate the solvents, and the resulting matrix is transferred to a final polyester carrier. After cutting to the desired size, the products are packaged in heat-sealable sachets.

EXAMPLE 7

201.4 g of diethyl phthalate, 201.1 g of SURFADONE® LP 300, 340.1 g of ODM, 40 g of Es, 80 g of NETA, 60 g of PVP/VA-S-630 and 1080.2 g of LEVAPREN® 500 HV are introduced into a reactor at 75° C. and the mixture obtained is stirred. 1999.8 g of ethyl acetate are then incorporated and the mixture is stirred, still at about 75° C., for a minimum of 4 hours, until the EVA copolymer has completely dissolved. The mixture obtained is allowed to degas. It is coated onto a temporary siliconized polyester carrier at a temperature of 50° C. so as to form a deposit of (100±10) g/m². The coated product is then placed in a drying tunnel at a temperature varying from 60 to 80° C. so as to evaporate the solvents, and the resulting matrix is transferred to a final polyester carrier. After cutting to the desired size, the products are packaged in heat-sealable sachets.

EXAMPLE 8

0.62 g of Es, 1.5 g of NETA, 3 g of SURFADONE® LP 300, 4.5 g of ODM, 3 g of diethyl phthalate, 0.3 g of PVP/VA-S-630, 10 g of ethanol and 40.5 g of ethyl acetate are introduced into a 250 ml beaker. The mixture obtained is heated at a temperature of between 65 and 75° C., with stirring, until the VA/VP copolymer has completely dissolved. 17.1 g of LEVAPREN® 600 HV are then introduced in portions and the mixture obtained is stirred for about 50 minutes, with continued heating at between 65 and 75° C., until the EVA copolymer has completely dissolved. The dry extract is readjusted to 50% by weight and the mixture obtained is allowed to degas. It is coated onto a temporary siliconized polyester carrier at a temperature of between 65 and 75° C. so as to form a deposit of (100±10) g/m². The coating obtained is heated at 70° C. for a minimum of 15 minutes in order to evaporate the solvents, and the resulting matrix is transferred to a final polyester carrier. After cutting to the desired size, the products are packaged in heat-sealable sachets.

EXAMPLE 9

The procedure is analogous to that of Example 1 except that only one hormone, namely NETA, is introduced in this case. 1.2 g of NETA, 3 g of SURFADONE® LP 300, 7.5 g of ODM, 1.5 g of diethyl phthalate, 40.5 g of ethyl acetate and 16.8 g of LEVAPREN® 500 HV are therefore used here.

EXAMPLE 10

The procedure is analogous to that of Example 9 except that 4.8 g of NETA, 19.2 g of SURFADONE® LP 300, 20.4 g of ODM, 6 g of diethyl phthalate, 162 g of ethyl acetate and 69.6 g of LEVAPREN® 600 HV are used in this case.

EXAMPLE 11

1.8 g of NETA, 4.8 g of SURFADONE® LP 300, 5.1 g of ODM, 3 g of diethyl phthalate and 40.5 g of ethyl acetate are introduced into a 250 ml beaker and the whole is heated to about 75° C., with stirring. 12 g of LEVAPREN® 600 HV and 3 g of LEVAPREN® 400 are then introduced in small portions and the mixture is stirred for about one hour, still at 75° C., until the EVA copolymer has completely dissolved. The dry extract is readjusted to 50% by weight and 0.6 g of PVP/VA-S-630 in 50% by weight ethanolic solution is introduced. The whole is stirred and the mixture obtained is allowed to degas. It is coated onto a temporary siliconized polyester carrier at a temperature of between 65 and 75° C. so as to form a deposit of 100±10 g/m². The coating obtained is heated at 70° C. for at least 15 minutes in order to evaporate the solvents. The resulting matrix is then transferred to a final polyester carrier. After cutting to the desired size, the products are packaged in heat-sealable sachets.

EXAMPLE 12

0.93 g of Es, 3 g of SURFADONE® LP 300, 3.9 g of ODM, 3 g of diethyl phthalate, 0.6 g of KOLLIDON VA-64 (a vinyl acetate/N-vinyl-2-pyrrolidone copolymer containing 37.7% by weight of vinyl acetate, marketed by BASF), 37.5 g of ethyl acetate and 3 g of ethanol are introduced into a 250 ml beaker. The whole is heated at 75° C., with stirring, until the KOLLDON VA-64 has completely dissolved. 18.6 g of LEVAPREN® 600 HV are then introduced in small fractions and the mixture is stirred for about 1 hour until the EVA copolymer has completely dissolved. The dry extract is readjusted to 50% by weight and the mixture obtained is allowed to degas. It is coated onto a temporary siliconized polyester carrier at a temperature of between 65 and 75° C. so as to form a deposit of (100±10) g/m². The coating obtained is then heated at 70° C. for at least 15 minutes in order to evaporate the solvents. The resulting matrix is then transferred to a final polyester carrier. After cutting to the desired size, the products are packaged in heat-sealable sachets.

EXAMPLE 13

The procedure is analogous to that of Example 12 except that a second hormone, namely NETA, is introduced in this case. 1.5 g of NETA, 0.62 g of Es, 4.8 g of SURFADONE® LP 300, 5.1 g of ODM, 1.5 g of diethyl phthalate, 0.3 g of KOLLIDON VA-64, 37.5 g of ethyl acetate, 3 g of ethanol and 16.2 g of LEVAPREN® 600 are therefore used here.

EXAMPLE 14

The procedure is analogous to that of Example 11 except that only one solvent, namely ethyl acetate, is employed; 1.8 g of NETA, 3.9 g of SURFADONE® LP 300, 5.1 g of ODM, 3 g of diethyl phthalate, 40.5 g of ethyl acetate, 15.9 g of LEVAPREN® 600 HV and 0.6 g of PVP/VA-S-630 are used in this case.

TESTS

The yields of the devices according to the invention are determined on the basis of measurements of the quantities of hormone(s) released in 24 hours in an ex vivo skin model.

This was done by carrying out ex vivo permeation tests on abdominal skin from male nude mice according to the following protocol.

The quantities of hormone(s) released by a transdermal device with a surface area of 2.54 cm², previously punched out and placed on a 3.14 cm² disk of abdominal skin from a male nude mouse, are measured in a static glass cell which is temperature-controlled at 37° C. and has a reception compartment with a volume of 11.5 ml, this reception compartment containing an isotonic solution/PEG 400 mixture (75/25 v/v) as the reception phase.

In view of the variability of results associated with the intrinsic permeability of skin samples, each permeation test for a sample of transdermal device is performed on a minimum number of 3 to 5 skin samples.

The result given is the mean obtained for each device on the basis of these tests. The ratio of this mean value of the quantities of hormone(s) released after 24 hours of kinetics to the initial quantity of hormone(s) contained in the device makes it possible to evaluate the 24-hour yield of the transdermal systems according to the invention.

For comparison purposes, the quantities of hormones released in 24 hours by the only currently available product comprising both an estrogen and a progestin, namely the device marketed under the trade mark ESTRAGEST® TTS by CIBA-GEIGY, were determined in the same manner. Said device is moreover the only commercial transdermal system to contain a progestin component.

The ESTRAGEST® TTS device is formed of two adjacent reservoirs containing a total of 10 mg of 17β-estradiol and 30 mg of NETA, each reservoir containing a mixture of 5 mg of 17β-estradiol and 15 mg of NETA.

The skin permeation measurements are made according to the same protocol on only one of the two reservoirs, placed on a 3.14 cm² skin sample. The initial quantities of hormones contained in this reservoir are converted to the initial quantity of hormones per unit surface area, expressed in μg/cm².

The ratio of the mean value of the quantities of 17β-estradiol or NETA released in 24 hours to the initial quantity contained in the reservoir makes it possible to obtain the 24-hour yields of Es or NETA.

The results obtained have been collated in Table I for the devices according to the invention containing an estrogen and a progestin, and in Table II for the devices containing a progestin only.

A comparison was also made between the yield of 17β-estradiol obtained in 24 hours from a device according to the invention and the yield of the only matrix device based on EVA copolymer which is currently on the market, namely the product OESCLIM®. This was done, always according to the same protocol, by carrying out ex vivo permeation tests on abdominal skin from male nude mice using 2.54 cm$^2$ samples of OESCLIM®. Several series of tests carried out with this matrix device show a mean initial value of 17β-estradiol per unit surface area of 452.7 μg/cm$^2$ and a quantity of 17β-estradiol released after 24 hours of 14.2 μg/cm$^2$ in this skin model.

Table III shows the yields calculated for the devices according to the invention of Examples 1, 2, 3, 6 and 12, considering only 17β-estradiol, and for the product OESCLIM®.

Figure 1:
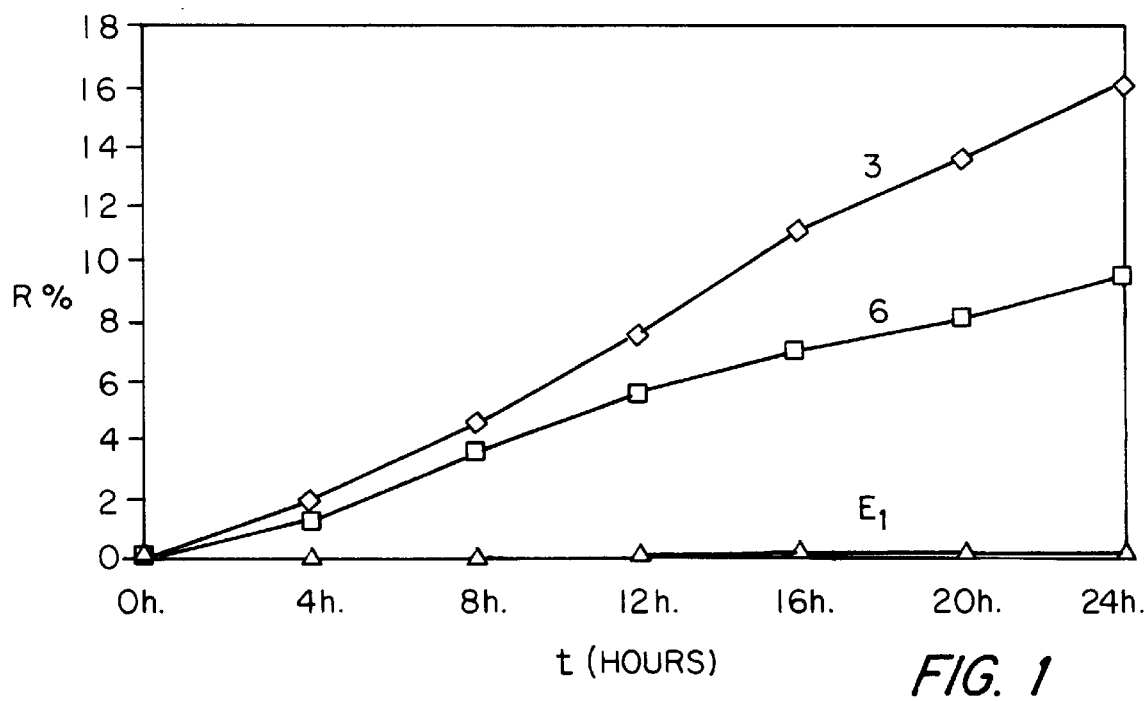
FIG. 1 shows the comparison (in the system R/t) between curves 3, 6 and $E_1$ relating to the yield of the release of 17β-estradiol, said curves being obtained respectively with the products of Examples 3 and 6 according to the invention and a reference transdermal product known under the name ESTRAGEST® TTS and marketed by CIBA-GEIGY (identified here as $E_1$)
Figure 2:
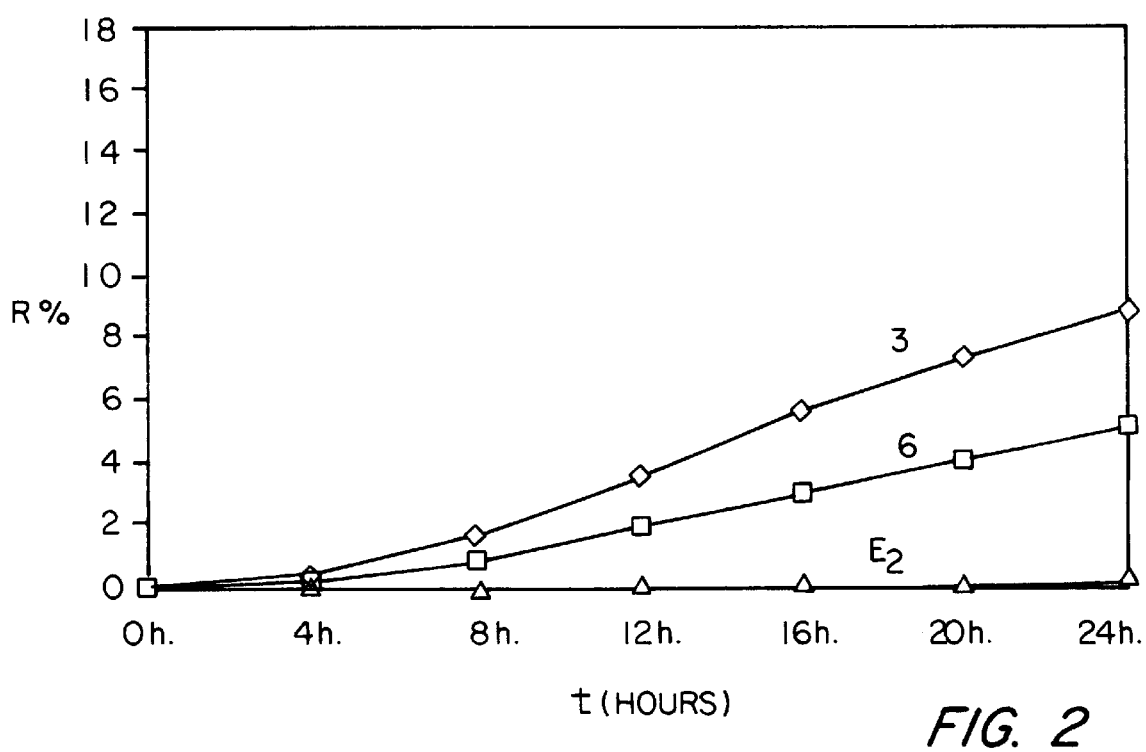
FIG. 2 shows the comparison (in the system R/t) between curves 3, 6 and $E_2$ relating to the yield of the release of NETA, said curves being obtained respectively with the products of Examples 3 and 6 according to the invention and said ESTRAGEST® TTS (identified here as $E_2$)

In the case of a matrix containing both 17β-estradiol and NETA, Table I illustrates the advantages of the systems according to the invention over the above-mentioned product ESTRAGEST® TTS. It is seen in this case, as shown by curves 3 and 6 in FIGS. 1 and 2, that the yields of the devices according to the invention, in respect of 17β-estradiol as well as NETA, are always significantly higher than those of the ESTRAGEST® TTS system, the initial quantities being smaller by factors of 8 and 12 respectively.

Furthermore, Table I shows that, in the case of 17β-estradiol, the yields are on average 25 to 80 times greater than that of ESTRAGEST® TTS and that, in the case of NETA, the yields are 20 to 50 times greater than that of ESTRAGEST® TTS.

More precisely, the comparison with ESTRAGEST® TTS is as follows:

for Example 1 a yield 47 times greater for Es and 29 times greater for NETA, for Example 2 a yield 55 times greater for Es and 32 times greater for NETA, for Example 3 a yield 81 times greater for Es and 52 times greater for NETA, for Example 4 a yield 36 times greater for Es and 29 times greater for NETA, for Example 5 a yield 26 times greater for Es and 18 times greater for NETA, for Example 6 a yield 48 times greater for Es and 31 times greater for NETA, for Example 7 a yield 29 times greater for Es and 18 times greater for NETA, for Example 8 a yield 38 times greater for Es and 23 times greater for NETA, for Example 13 a yield 75 times greater for Es and 50 times greater for NETA.

These large differences again demonstrate the advantages of the invention, namely the ability to make considerable cost savings by using less product for the desired therapeutic purpose, the avoidance of possible problems of crystallization and incompatibility in the matrix, and hence simplification of the development of the systems and the manufacture particularly of high-performance and commercially acceptable matrix systems for the administration of an estrogen component and a progestin component.

Depending on the particular case, the VA/VP copolymer used in Examples 6–8 and 13 is useful for improving the adhesion of the devices, the solubility of the hormones in the matrix or, surprisingly, the skin irritation phenomena which may appear during use. According to the invention, in view of the quantities used, the presence of the VA/VP copolymer does not detract from obtaining good yields.

Likewise, equally good results are always obtained in the case of a mixture of two EVAs with different vinyl acetate contents (Example 4).

Similarly, analogous results are obtained in the case of systems containing Es only or NETA only, as illustrated on the one hand in FIGS. 3 and 4 and on the other hand in Tables II and III.

The results in Table II show that the quantities of NETA released are always greater than that released by the ESTRAGEST® TTS device, despite the 12-fold lower concentrations.

Analysis of the yields in Table II shows that, compared with the ESTRAGEST® TTS device, the yields of NETA are 26 times, 39 times, 25 times and 48 times greater for the products of Examples 9, 10, 11 and 14 respectively.

The results in Table III also demonstrate the advantages of the devices according to the invention over the product OESCLIM® in the case of 17β-estradiol. Compared with the product OESCLIM®, which is the only EVA-based matrix system currently on the market, it is again found that the yields of the devices according to the invention, whether for Examples 1, 2, 3 and 6, which contain 17β-estradiol and NETA, or for Example 12, which like OESCLIM® contains 17β-estradiol only, are always 3 to 5 times greater in the best case. This result is also illustrated by curves 2 and 8 (relating to Examples 2 and 8) in FIG. 3.

Likewise, curves 3 and 6 in FIG. 4 show that the quantities of 17β-estradiol released by the devices according to the invention are always significantly greater than that released by the product OESCLIM®, the quantities being 2.3 times smaller.

In terms of the advantages of the devices according to the invention, the conclusions drawn from Table I in the case of the administration of both hormones are therefore again obvious and identical in the case of the administration of only one hormone.

TABLE I

|    |          | Ex. 1 | Ex. 2 | Ex. 3 | Ex. 4 | Ex. 5 | Ex. 6 | Ex. 7 | Ex. 8 | Ex. 13 | ESTRAGEST® TTS |
|----|----------|-------|-------|-------|-------|-------|-------|-------|-------|--------|-----------------|
| Es | $Q_0$    | 212.6 | 200.8 | 192.9 | 192.9 | 200.6 | 192.9 | 212.6 | 204.7 | 181    | 1570            |
|    | $Q_{24}$ | 19.9  | 22    | 31.1  | 14.1  | 10.5  | 18.7  | 12.5  | 15.5  | 27.3   | 3.1             |
|    | R        | 9.4   | 11    | 16.2  | 7.3   | 5.2   | 9.7   | 5.9   | 7.6   | 15     | 0.2             |

TABLE I-continued

|  |  | Ex. 1 | Ex. 2 | Ex. 3 | Ex. 4 | Ex. 5 | Ex. 6 | Ex. 7 | Ex. 8 | Ex. 13 | ESTRAGEST® TTS |
|---|---|---|---|---|---|---|---|---|---|---|---|
| NETA | $Q_0$ | 421.2 | 401.6 | 385.8 | 484.2 | 404.4 | 385.8 | 429.1 | 511.8 | 449 | 4790 |
|  | $Q_{24}$ | 20.9 | 21.9 | 34.2 | 24 | 12.6 | 20.2 | 13.2 | 20 | 38.2 | 8.2 |
|  | R | 5 | 5.5 | 8.9 | 5 | 3.1 | 5.2 | 3.1 | 3.9 | 8.5 | 0.17 |

$Q_{24}$: Quantity of Es or NETA released in 24 hours, expressed in $\mu g/cm^2$
$Q_0$: Initial quantity of Es or NETA, expressed in $\mu g/cm^2$
R: Yield expressed as a percentage (R = 100 $Q_{24}/Q_0$)

TABLE II

|  |  | Ex. 9 | Ex. 10 | Ex. 11 | Ex. 14 | ESTRAGEST® TTS |
|---|---|---|---|---|---|---|
| NETA | $Q_0$ | 397.6 | 413.3 | 586.7 | 590 | 4790 |
|  | $Q_{24}$ | 17.8 | 27.9 | 24.8 | 47.8 | 8.2 |
|  | R | 4.5 | 6.7 | 4.2 | 8.1 | 0.17 |

$Q_{24}$: Quantity of NETA released in 24 hours, expressed in $\mu g/cm^2$
$Q_0$: Initial quantity of NETA, expressed in $\mu g/cm^2$
R: Yield expressed as a percentage (R = 100$Q_{24}/Q_0$)

TABLE III

|  |  | Ex. 1 | Ex. 2 | Ex. 3 | Ex. 6 | Ex. 12 | OESCLIM® |
|---|---|---|---|---|---|---|---|
| Es | $Q_0$ | 212.6 | 200.8 | 192.9 | 192.9 | 295 | 452.7 |
|  | $Q_{24}$ | 19.9 | 22 | 31.3 | 18.7 | 27.5 | 14.2 |
|  | R | 9.4 | 11 | 16.2 | 9.7 | 9.3 | 3.1 |

$Q_{24}$: Quantity of Es released in 24 hours, expressed in $\mu g/cm^2$
$Q_0$: Initial quantity of Es, expressed in $\mu g/cm^2$
R: Yield expressed as a percentage (R = 100$Q_{24}/Q_0$)

We claim:

1. A transdermal matrix system for the transdermal administration of at least one hormone, said system having a carrier and an adhesive matrix, said matrix comprising:
   (a) 39 to 61 parts by weight of ethylene/vinyl acetate copolymer,
   (b) 12 to 17 parts by weight of 2-octyldodecyl myristate,
   (c) 5 to 17 parts by weight of diethyl phthalate,
   (d) 10 to 16 parts by weight of a compound selected from N-alkyl-2-pyrrolidones in which the alkyl group is a $C_4$–$C_{15}$ group, and
   (e) 1 to 12 parts by weight of at least one hormone selected from the group consisting of estrogen components and progestin components.

2. A transdermal matrix system according to claim 1 wherein said adhesive matrix also comprises 1 to 10 parts by weight of a vinyl acetate/N-vinyl-2-pyrrolidone (VA/VP) copolymer.

3. A transdermal matrix system according to claim 2 wherein the vinyl acetate/N-vinyl-2-pyrrolidone copolymer has a vinyl acetate content of between 30 and 70% by weight, based on the weight of the copolymer.

4. A transdermal matrix system according to claim 1 wherein the N-alkyl-2-pyrrolidone is N-dodecyl-2-pyrrolidone.

5. A transdermal matrix system according to claim 1 wherein the ethylene/vinyl acetate copolymer has a vinyl acetate content of between 30 and 75% by weight based on the weight of the copolymer.

6. A transdermal matrix system according to claim 1 wherein the hormone is an estrogen component.

7. A transdermal matrix system according to claim 1 wherein the hormone is a progestin component.

8. A transdermal matrix system according to claim 1 wherein the system contains a mixture of an estrogen component and a progestin component.

9. A method of preparing a transdermal matrix system comprising the steps of:
   introducing diethyl phthalate, N-alkyl-2-pyrrolidone, 2-octyldodecyl myristate, at least one hormone selected from the group consisting of estrogen components, progestin components and mixtures thereof, optionally VA/VP copolymer, and EVA successively into a reactor to form a mixture and stirring the mixture;
   incorporating a solvent or solvent system into the mixture at a temperature below the boiling point of the solvent or solvent system used and stirring, still at the same temperature, until the EVA has dissolved and said mixture has become homogeneous;
   coating the homogeneous mixture onto a non-stick temporary carrier, at a temperature of between 50 and 70° C., to give a deposit of 50 to 300 g/m² on said carrier;
   heating the coating so as to evaporate the solvent to form a dry matrix; and
   transferring the dry matrix to a final carrier.

10. A method for treating the symptoms of menopause or osteoporosis using a transdermal matrix system according to any one of claims 1 to 8.

11. A system according to claim 2 wherein the matrix comprises the following for a total of 100 parts by weight:
   54 parts by weight of ethylene/vinyl acetate copolymer;
   17 parts by weight of 2-octyldodecyl myristate;
   5 parts by weight of diethyl phthalate;
   16 parts by weight of N-dodecyl-2-pyrrolidone;
   2 parts by weight of 17β-estradiol;
   5 parts by weight of norethisterone acetate; and
   1 part by weight of a vinyl acetate/N-vinyl-2-pyrrolidone (VA/VP) copolymer.

12. A system according to claim 2 wherein the matrix comprises the following for a total of 100 parts by weight:
   62 parts by weight of ethylene/vinyl acetate copolymer;
   13 parts by weight of 2-octyldodecyl myristate;
   10 parts by weight of diethyl phthalate;
   10 parts by weight of N-dodecyl-2-pyrrolidone;
   3 parts by weight of 17β-estradiol; and
   2 parts by weight of a vinyl acetate/N-vinyl-2-pyrrolidone (VA/VP) copolymer.

13. A system according to claim 2 the matrix comprises the following for a total of 100 parts by weight:
   53 parts by weight of ethylene/vinyl acetate copolymer;
   17 parts by weight of 2-octyldodecyl myristate;
   10 parts by weight of diethyl phthalate;
   13 parts by weight of N-dodecyl-2-pyrrolidone;
   6 parts by weight of norethisterone acetate; and 1 part by weight of a vinyl acetate/N-vinyl-2-pyrrolidone (VA/VP) copolymer.

14. A transdermal matrix system according to claim 2 wherein the N-alkyl-2-pyrrolidone is N-dodecyl-2-pyrrolidone.

15. A transdermal matrix system according to claim 3 wherein the N-alkyl-2-pyrrolidone is N-dodecyl-2-pyrrolidone.

16. A transdermal matrix system according to claim 2 wherein the ethylene/vinyl acetate copolymer has a vinyl acetate content of between 30 and 75% by weight based on the weight of the copolymer.

17. A transdermal matrix system according to claim 3 wherein the ethylene/vinyl acetate copolymer has a vinyl acetate content of between 30 and 75% by weight based on the weight of the copolymer.

18. A transdermal matrix system according to claim 2 wherein the hormone is an estrogen component.

19. A transdermal matrix system according to claim 3 wherein the hormone is an estrogen component.

20. A transdermal matrix system according to claim 2 wherein the hormone is a progestin component.

21. A transdermal matrix system according to claim 3 wherein the hormone is a progestin component.

22. A transdermal matrix system according to claim 2 wherein the system contains a mixture of an estrogen component and a progestin component.

23. A transdermal matrix system according to claim 3 wherein the system contains a mixture of an estrogen component and a progestin component.

* * * * *